United States Patent [19]

Tsai et al.

[11] Patent Number: 5,206,162
[45] Date of Patent: Apr. 27, 1993

[54] PROCESS FOR MAKING D-AMINOACYLASE

[75] Inventors: Ying C. Tsai; Chyuan S. Lin; Ching P. Tseng; Yunn B. Yang, all of Taipei, Taiwan

[73] Assignee: National Science Council of Republic of China, Taipei, Taiwan

[21] Appl. No.: 778,240

[22] Filed: Oct. 17, 1991

[51] Int. Cl.$^5$ .......................... C12R 1/05; C12N 9/80; C12N 9/78
[52] U.S. Cl. .................. 435/228; 435/71.1; 435/195; 435/227; 435/829
[58] Field of Search ............... 435/227, 228, 233, 829, 435/232, 71.1, 195

[56] References Cited

U.S. PATENT DOCUMENTS 4,981,799  1/1991  Takahashi et al. ................ 435/233

OTHER PUBLICATIONS

Sugie, et al., "Purification and properties, ... ", (1978), pp. 107-113, Agric. Bio. Chem. 42(1).
Kubo, et al., "Deacetylation of PS-5, ... ", (Jun. 1980), pp. 556-565 Journal of Antibiotics.
Yang et al., "Purification and Characterization of ... ", Applied and Environmental Microbiology, vol. 57, No. 4, pp. 1259-1260 USA Apr. 1991.

Primary Examiner—Herbert J. Lilling
Attorney, Agent, or Firm—Jacobson, Price, Holman & Stern

[57] ABSTRACT

A process for making D-aminoacylse includes adding 1% N-acetyl-DL-amino acid preferably N-acetyl-DL-methionine and N-acetyl-DL-leucine in a culturing medium incubated with bacteria selected from the strain of *Alcaligenes faecalis* for culturing the bacteria and for inductively promoting an enzyme reaction to produce the D-aminoacylase which is able to hydrolyze D-amino acids and unable to hydrolyze L-amino acids.

1 Claim, 4 Drawing Sheets

PROCESS FOR MAKING D-AMINOACYLASE

BACKGROUND OF THE INVENTION

D-Amino acids may serve as intermediates for producing β-Lactam antibiotics, such as penicillin or cephalosporin; insecticides or pesticides. The conventional synthetic amino acids are generally racemized mixtures containing dextro- and levo- amino acids which should be separated by optical resolution to obtain D-form and L-form amino acids.

Among those conventional methods of optical resolution for obtaining the D-form or L-form amino acid, an enzyme method is found to be most economic and feasible by utilizing the high stereo specificity of the enzyme for the resolution of D-form and L-form amino acid. Similarly, a D-aminoacylase of high stereospecificity may also be utilized for making D-amino acid.

M. Sugie and H. Suzuki had reported in their publication, entitled "Purification and properties of D-aminoacylase of *Streptomyces olivaceus*", Agri, Biol. Chem. 42:107–113 (1978), the preparation of D-aminoacylase by the bacteria of *Streptomyces olivaceus*. From Table II of M. Sugie's publication, a relative hydrolysis rate of N-acetyl-L-Met to N-acetyl-D-Met is calculated to be: 60/689 = 9% as summarized in Table 4 of this application. Also, K. Kubo, T. Ishikura and Y. Fukagawa disclosed a process for making D-aminoacylase by Pseudomonas sp. 1158 in their publication entitled "Deacetylation of PS-5, a new β-lactam compound II, Separation and Purification of L and D amino acid acylase from Pseudomonas sp. 1158", J. Antibiotics, 33:556–565 (1980). From Table 3 of Kubo's publication, a relative hydrolysis rate of N-acetyl-L-Met/N-acetyl-D-Met is calculated to be: 10.3/100 = 10.3% also summarized in Table 4 of this application.

However, the D-aminoacylase made from either *Streptomyces olivaceus* or Pseudomonas sp. 1158 shows poor stereospecificity, capable of hydrolyzing N-acyl-L-amino acid such as N-acetyl-L-methionine to thereby reduce the yield of D-amino acid when made by a resolution process.

The present inventors have found the drawbacks of such conventional enzyme method for making D-aminoacylase and invented the present method by using bacteria of the *Alcaligenes faecalis* species.

SUMMARY OF THE INVENTION

The object of the present invention is to provide a process for preparing D-aminoacylase by adding N-acyl-DL-amino acids as nutrients for cell growth for the bacteria of Alcaligenes faecalis, and as inductive reagents for stimulating the production of D-aminoacylase.

Curve A: pH 5.0–pH 8.0, 0.1M $K_2HPO_4$-$KH_2PO_4$ buffer,

Curve B: pH 7.5–pH 9.0, 0.1M Tris-HCl buffer, and

Curve C: pH 8.5–pH 11.0, 0.1M $Na_2CO_3$-$NaHCO_3$ buffer.

Figure 4:
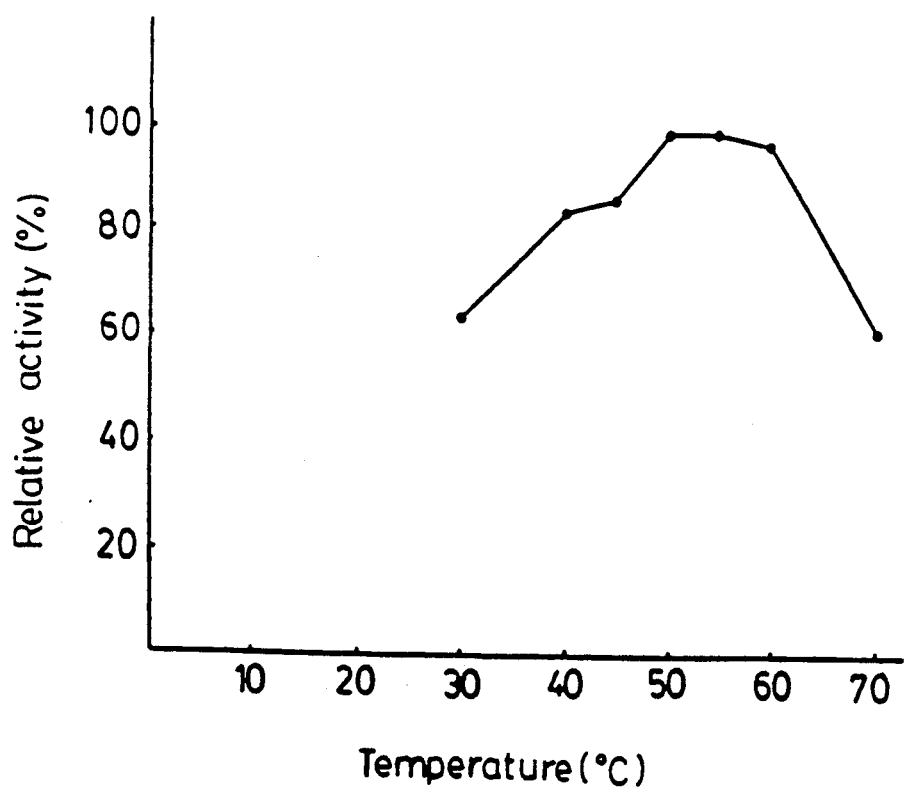

FIG. 4 shows the effect of temperature on D-aminoacylase activity assayed in buffer by ninhydrin method in which the enzyme activity was assayed at various temperatures in buffer A by the ninhydrin method.

DEPOSIT OF THE MICROORGANISM

The microorganism *Alcaligenes faecalis* DA 1 was deposited on Aug. 2, 1991 at the Culture Collection & Research Center, Food Industry Research & Development Institute (CCRC), 233, Shih-Pin Road, Hsin Chu City, Taiwan, Republic of China, and was given accession number CCRC 14817.

DETAILED DESCRIPTION

This invention relates to a process for making D-aminoacylase by means of *Alcaligenes faecalis* strain of the Alcaligenes.

The properties of D-aminoacylase and the process for producing the enzyme will be described in detail hereinafter.

The activity of D-aminoacylase obtained by the method of this invention may be measured in accordance with Rosen method by using suitable amount of enzyme to decompose N-acetyl-D-methionine, of which the produced D-methionine may be quantitatively measured by D-amino acid oxidase or by ninhydrin method. [Note: H. Rosen, A modified ninhydrin colorimetric analysis for amino acids. Arch. Biochem. Biophys. 67:10–15 (1957)].

The activity unit of enzyme of this invention is defined herewith as the enzyme quantity required for decomposing 10 mM N-acetyl-D-methionine solution for releasing 1μ mole D-methionine per minute at 37° C.

I. PROPERTIES

The several properties of D-aminoacylase are described as follows:

A. Effect and substrate specificity

The D-aminoacylase of this invention (hereinafter simply designated as "the acylase") may hydrolyze N-acyl-D-amino acids, but only slightly hydrolyze the N-acyl-L-amino acids. The reaction of the acylase with N-acetyl-D-methionine is the strongest in view of the specificity data as shown in Table 1.

TABLE 1

Substrate Specificity

| Substrate | Relative Activity | |
|---|---|---|
| | D-form | L-form |
| N-acetyl-methionine | 100 | 0.8 |
| N-acetyl-phenylalanine | 80 | 0.8 |
| N-chloroacetyl-valine | 42 | 0.6 |
| N-acetyl-leuoine | 40 | 0.4 |
| N-acetyl-alanine | 14 | 0.7 |
| N-acetyl-tryptophan | 14 | 0 |
| N-acetyl-asparagine | 8 | 0 |
| N-acetyl-valine | 6 | 0 |
| N-acetyl-phenylglycine | 3 | 0 |

B. Thermal stability

Figure 1:
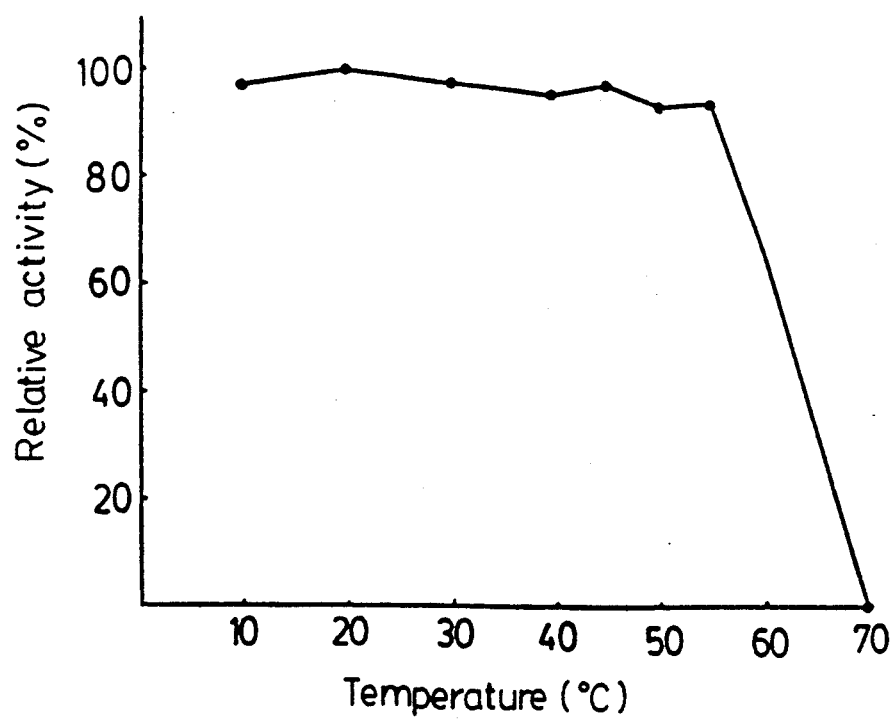
FIG. 1 is a diagram showing a relationship between the relative activity of D-aminoacylase and the temperature, indicating the thermal stability of D-aminoacylase effected by temperature in accordance with the present invention in which the enzyme was incubated at the indicated temperature for 30 minutes in buffer A, and the remaining activity was determined by the ninhydrin method.

The acylase is dissolved in 50 mM Tris-HCl pH 7.8 buffer and is kept for 30 minutes at different temperatures. The residual activity is measured at 37° C. by ninhydrin method to obtain the result as shown in FIG. 1. From the test result, the acylase is very stable under 55° C.

C. pH Stability

Figure 2:
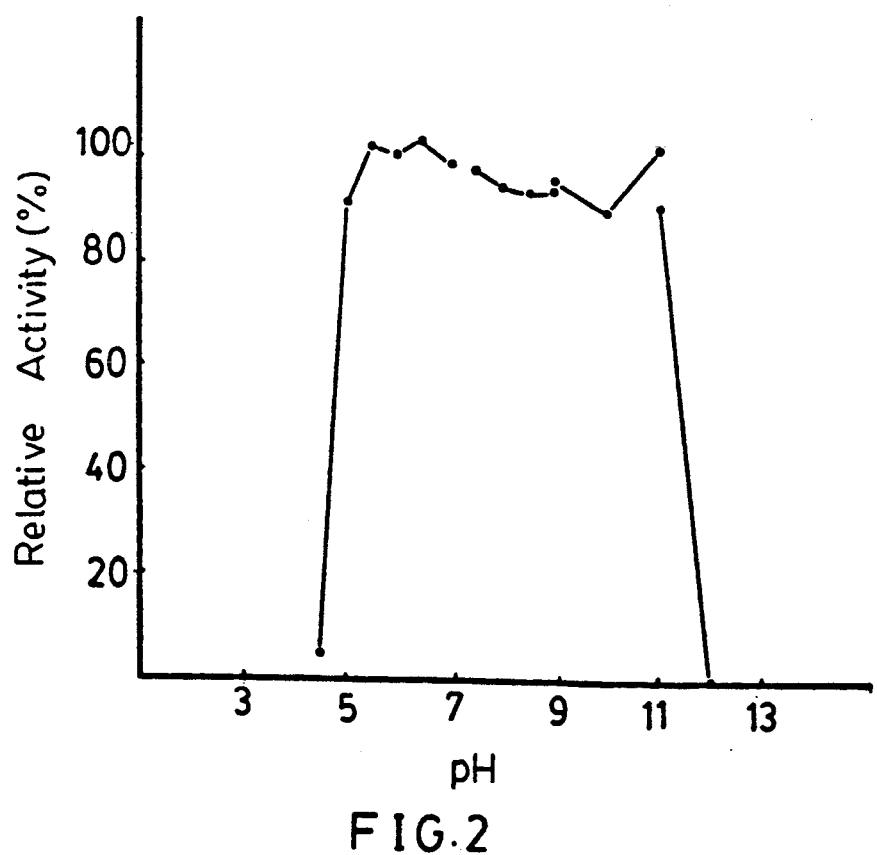
FIG. 2 shows a relationship between the relative activity of D-aminoacylase and the pH value, showing the stability of D-aminoacylase versus pH value in accordance with the present invention in which the enzyme was incubated in a buffer at the pH indicated. After incubation at 37° C. for 60 minutes, the residual activity was determined at pH 7.8. The buffer systems used were $CH_3COOH$-$CH_3COONa$ (pH 4.5–pH 5.5), $K_2HPO_4$-$KH_2PO_4$ (pH 5.5–pH 7.0), Tris-HCl (pH 7.5–pH 9.0), $Na_2CO_3$-$NaHCO_3$ (pH 9.0–pH 11.0) and $Na_2HPO_4$-NaOH (pH 11.0–pH 12.0).

The acylase enzyme is dissolved in buffers of different pH values and is kept for 60 minutes at 37° C. Under the situation of pH 7.8, the ninhydrin method is applied for measuring the residual activities as shown in FIG. 2. From the test result, it proves that the acylase of the present invention is very stable at pH value ranging from 6 to 11. The buffers used in this test are:

| | |
|---|---|
| $CH_3COOH$—$CH_3COONa$ | (pH 4.5–5.5), |
| $K_2HPO_4$—$KH_2PO_4$ | (pH 5.5–7.0), |
| Tris—HCl | (pH 7.5–9.0), |
| $Na_2CO_3$—$NaHCO_3$ | (pH 9.0–11.0), |
| $Na_2HPO_4$—NaOH | (pH 11.0–12.0) |

D. Reaction pH

Figure 3:
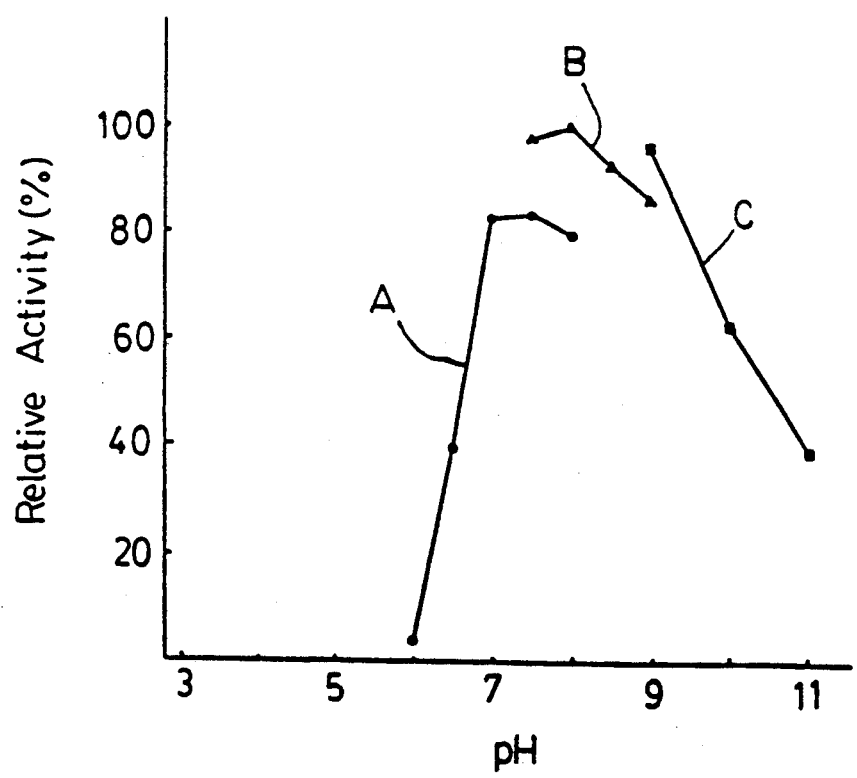
FIG. 3 shows the relationship between the relative activity of D-aminoacylase and the pH value under different buffers in accordance with the present invention in which the enzyme activity was determined at 37° C. by the ninhydrin method, and the three curves A, B and C, respectively, correspond to the following buffers.

Under 37° C. and different pH values of buffers, the acylase activities are measured by ninhydrin method as shown in FIG. 3, from which the optimum reaction pH value of the acylase is about 8.0.

E. Reaction temperature

Within pH 7.8 50 mM Tris-HCl buffer and at different temperatures, the enzyme activities of the invention are measured by ninhydrin method as shown in FIG. 4, from which the optimum reaction temperature is ranging about 50°–60° C.

F. Molecular weight

The molecular weight of D-aminoacylase of the present invention is about 55,000 which is measured by Gel. filtration method by using HPLC column G 3000 SW, or measured by SDS-PAGE method.

G. Isoelectric point

By using polyacrylamide gel for performing isoelectrofocusing, the isoelectric point of the acylase is 5.35.

H. The influence of metallic ions

The acylase of the present invention is dissolved in a 50 mM Tris-HCl buffer (pH 7.8), having each buffer dissolved with each metallic ion of 1 mM concentration of the plural different metallic ions, and is kept for 30 minutes at 37° C. for testing residual activities by ninhydrin method for obtaining the results as shown in Table 2, from which the acylase is inhibited by each metallic ion with different degrees:

TABLE 2

Influence of metallic ions on D-aminoacylase activities

| Metallic Ions | Residual activities % |
|---|---|
| None | 100 |
| $BaCl_2$ | 99 |
| $CaCl_2$ | 99 |
| $CoCl_2$ | 96 |
| $MgCl_2$ | 95 |
| $NiCl_2$ | 89 |
| $SrCl_2$ | 87 |
| $MnCl_2$ | 70 |
| $FeCl_2$ | 60 |
| $CuCl_2$ | 15 |
| $ZnCl_2$ | 0 |
| $FeCl_2$ | 0 |
| $CdCl_2$ | 0 |
| $HgCl_2$ | 0 |

I. Influence by inhibitors

The acylase is dissolved in each pH 7.8, 50 mM Tris-HCl buffer containing different inhibitors of 1 mM and is kept at 37° C. for 30 minutes, which is then measured for its residual activity by ninhydrin method to obtain the result as shown in Table 3, from which it indicates that the enzyme of this invention is inhibited by: p-chloromercuibenzoic acid, EDTA, N-ethylmaleimide, and phenylglyoxal.

TABLE 3

Reagents influencing the D-aminoacylase activities

| Reagents | Residual activities % |
|---|---|
| p-chloromercuibenzoic acid | 0 |
| EDTA | 22 |
| N-ethylmaleimide | 36 |
| phenylglyoxal | 65 |
| iodoacetamide | 97 |
| sodium azide | 97 |

II. MICROORGANISM UTILIZED

The bacteria used in this invention for producing D-aminoacylase may be selected from the genus of Alcaligenes, in which a specific strain of *Alcaligenes faeclalis* DA-1 was isolated from soil by the inventors of this application to have the following characteristics or properties of bacteria:

A: Forms:
  Cell shape: Oval bacilli.
  Cell size: 0.6–2.0 μm × 0.5–1.0 μm
  Motility: motile bacterium with peritruchous flagella.
  Spore formation: no spore formed.
  Gram stain: negative.

B. Culturing characteristics:
  Growth temperature range: 8°–42° C.
  Optimum growth temperature: 25°–37° C.
  Growth pH range: 4.7–10.0
  Table salt growth limit: 7%
  Oxygen demand: obligately aerobic C. Physiological properties:

| | |
|---|---|
| Catalase | Positive |
| Cytochrome oxidase | Positive |
| Lysine decarboxylase | Negative |
| Ornithine decarboxylase | Negative |
| Tryptophan deaminase | Negative |
| Voges-Proskauer test | Negative |

| -continued | |
|---|---|
| Methyl red reaction | Negative |
| Litmus milk reaction | Positive |
| Nitrate reduction | Positive |
| Indole formation | Negative |
| $H_2S$ formation | Negative |
| Dehydroacetone formation | Negative |
| Mucoid formation | Negative |
| Citrate utilization | Positive |
| Malonic acid utilization | Negative |
| Gluconic acid utilization | Positive |
| Urea decomposing | Negative |
| Starch decomposing | Negative |
| Casein decomposing | Negative |
| Gelatin decomposing | Negative |
| Arginine decomposing | Negative |
| DNA decomposing | Negative |
| Agar decomposing | Negative |
| Tween 80 decomposing | Negative |
| Glucose utilization | Negative |
| Fructose utilization | Negative |
| Lactose utilization | Negative |
| Maltose utilization | Negative |
| Sucrose utilization | Negative |
| Xylose utilization | Negative |
| Arabinose utilization | Negative |
| Sorbitol utilization | Negative |
| Mannitol utilization | Negative |
| Ethanol utilization | Positive |

From the above-mentioned properties, the DA-1 strain belongs to a strain of *Alcaligenes faecalis.*

III. PREPARATION OF D-AMINOACYLASE

The preparation of D-aminoacylase by using the *Alcaligenes faecalis* strain is described hereinafter:

When culturing, any culturing medium suitable for Alcaligenes bacteria growth may be used for producing D-aminoacylase. The most popular nitrogen sources are selected from: yeast extract, peptone, meat extract, and soymeal; while the carbon source may be selected from organic acids; and the inorganic salts may be added with: $K_2HPO_4$, $MgSO_4$, NaCl, etc.

Even solid culturing method is applicable, the liquid culturing method is preferable. For instance, a jar fermentor may be applied for performing air-penetratable agitating cultivation. The culturing temperature is preferably ranging from 25° to 35° C.; pH value is ranging 7-9 and the culturing period is ranging 12-48 hours.

The bacteria cells are extracted, collected and stricken or broken by ultrasonic waves, from which the cells are ground by grinders such as miller homogenizer. Any enzymes capable of dissolving bacteria are used for dissolving the bacteria cells. And an organic solvent or surface active agent is provided for treating, and breaking the cells. The cell debris are centrifuged, filtered and removed for purifying the obtained enzyme, which is further purified by any purification methods, such as: ammonium sulfate fractionation, solvent precipitation, and chromatographies.

When culturing the bacterial cells, suitable amount of N-acyl-D-amino acid is added for promoting the enzyme production. It is preferable to add 1% (or so) N-acetyl-DL-methionine or N-acetyl-DL-leucine.

EXAMPLE 1

In 5 liters jar fermentor, 3 liters 1% N-acetyl-DL-leucine, 0.5% yeast extract, 0.5% peptone, 0.1% $K_2HPO_4$, and 0.05% $MgSO_4$ $7H_2O$ are added for providing a culturing medium having a pH of 7.8, and the *Alcaligenes faecalis* DA-1 bacteria are incubated into the fermentor for bacterial growth and enzyme production of the present invention.

After an overnight air-supplying agitation of 20 hours, the cells are suspended in 300 ml Tris-HCl buffer (50 mM, pH 7.8) and the cells are broken by ultrasonic waves. The cell debris are centrifuged and removed. The supernatant layer is then purified by Fractogel TSK DEAE-650 column chromatography (2.5×64 cm), and Fractogel TSK HW-50 column (1.6×110 cm) to obtain a pure product of D-aminoacylase having a specific activity of 580 units/mg.

The properties of D-aminoacylase produced by the present invention is further summarized in Table 4 to be compared with the prior arts of acylases by using *Streptomyces olivaceus* and Pseudomonas sp.1158 respectivell, from which the relative hydrolysis rate of N-acetyl-L-amino acid to N-acetyl-D-amino acid of this invention is less than the prior arts to denote that the acylase of this invention may hydrolyze the D-amino acid, but may only hydrolyze L-amino acid slightly to increase or dominate the yield of the D-amino acid in a resolution for making D-amino acid benificial for medical or agriculture uses.

TABLE 4
Comparison of this invention with prior arts

| D-aminoacylase Properties | Alcaligenes faecalis | S. olivaceus | Pseudomonas sp.1158 |
|---|---|---|---|
| Molecular weight | 55,000 | 45,000 | 100,000 |
| Isoelectric point | 5.35 | — | 4.95 |
| Optimum reaction pH | 8.0 | 7.0 | 7.0 |
| $Co^{++}$ influence | inhibited | promoted | promoted |
| N-acetyl-L-Methionine | | | |
| N-acetyl-D-Methionine relative hydrolysis rate | 0.8% | 9% | 10.3% |

The concentration of ingredients, such as N-acetyl-D-amino acid designated in this application is a weight-/volume percentage of grams weight of solute based on 100 ml volume of solution.

We claim:

1. A process for producing D-aminoacylase comprising adding 1% (weight/volume) of an N-acetyl-DL-amino acid selected from the group consisting of N-acetyl-DL-methionine and N-acetyl-DL-leucine to a culturing medium, culturing bacteria of the strain *Alcaligenes faecalis* DA-1 having accession number CCRC 14817 in said culturing medium, and recovering D-aminoacylase from the cultured bacteria;

said D-aminoacylase having properties including: a substrate specificity capable of hydrolyzing N-acetyl-D-amino acids and unable to hydrolyze N-acetyl-L-amino acids and having a relative activity of 0.8% for the reaction of said D-aminoacylase with N-acetyl-L-methionine with respect to a relative activity of 100% for the reaction of said D-aminoacylase with N-acetyl-D-methionine; a molecular weight of 55,000; an isoelectric point of 5.35; and being inhibited by metallic ions of mercuric, cupric and carbonyl ions and inhibited by p-chloromercuribenzoic acid, N-ethylmaleimide and EDTA.

* * * * *